United States Patent [19]

Langley et al.

[11] Patent Number: 5,492,646

[45] Date of Patent: Feb. 20, 1996

[54] POLYMERIC MATRIX PARTICLE COMPOSITIONS CONTAINING COACERVATE POLYMER SHELL

[75] Inventors: John G. Langley; Kenneth C. Symes; Kishor K. Mistry, all of West Yorkshire, United Kingdom

[73] Assignee: Allied Colloids Limited, United Kingdom

[21] Appl. No.: 150,016

[22] PCT Filed: May 14, 1992

[86] PCT No.: PCT/GB92/00867

§ 371 Date: Nov. 15, 1993

§ 102(e) Date: Nov. 15, 1993

[87] PCT Pub. No.: WO92/20771

PCT Pub. Date: Nov. 26, 1992

Related U.S. Application Data

[63] Continuation-in-part of Ser. No. 734,545, Jul. 23, 1991, Pat. No. 5,324,445, and a continuation-in-part of Ser. No. 398,083, Aug. 24, 1989, abandoned.

[30] Foreign Application Priority Data

| Jan. 19, 1988 | [GB] | United Kingdom | 8901182 |
| Aug. 24, 1988 | [GB] | United Kingdom | 8820062 |
| May 14, 1991 | [GB] | United Kingdom | 9110408 |

[51] Int. Cl.$^6$ ................................. C11D 3/386
[52] U.S. Cl. ............. 252/174; 252/174.12; 252/DIG. 12
[58] Field of Search ..................... 252/174, 174.12, 252/174.13, DIG. 12; 427/213.3

[56] References Cited

U.S. PATENT DOCUMENTS 3,843,557  10/1974  Fanger et al. .
4,677,003  6/1987  Redlich et al. .
4,777,089  11/1988  Takizawa et al. ................. 252/174.13
5,035,900  7/1991  Langley et al. .................... 424/484
5,281,357  1/1994  Morgan et al. .................... 252/174
5,324,445  6/1994  Langley et al. ................. 252/174.12

FOREIGN PATENT DOCUMENTS 0356239  2/1990  European Pat. Off. .
2156014  5/1973  France .

Primary Examiner—Olik Chaudhuri
Assistant Examiner—C. Everhart
Attorney, Agent, or Firm—Ostrolenk, Faber, Gerb & Soffen

[57] ABSTRACT

This invention relates to the encapsulation of active ingredient within polymeric material so as to protect the active ingredient from the ambient environment, for instance atmospheric moisture when the product is exposed to the air, or the liquid phase of a liquid detergent when the product is incorporated in such a detergent. A dispersion in oil of an aqueous solution of a matrix polymeric material containing enzyme or other active ingredient is subjected to distillation to provide a substantially anhydrous dispersion in oil of particles of matrix polymer containing active ingredient, and during or after the distillation the polymer solution is converted into a solid polymer. In the invention, we use a matrix polymer that is so hydrophobic that it partitions preferentially into the oil rather than into the aqueous solution of encapsulating polymer. Because the aqueous solution is incompatible with both the hydrophobic oil and the matrix polymer, there is increased tendency for the encapsulating shell to be formed around a layer of oil, rather than in direct contact with a matrix polymer particle.

27 Claims, No Drawings

POLYMERIC MATRIX PARTICLE COMPOSITIONS CONTAINING COACERVATE POLYMER SHELL

This application is a 371 of PCT application PCT/GB92/ 00867, filed May, 14, 1992 and a continuation-in-part of U.S. Ser. No. 734,545 filed 23rd Jul. 1991 by John Langley and Kenneth Symes (now U.S. Pat. No. 5,324,445) and a C-I-P of U.S. application Ser. No. 398,083 filed 24th Aug. 1989 by John Langley and Kenneth Symes (abandoned).

This invention relates to the encapsulation of active ingredient (especially detergent enzyme) within polymeric material so as to protect the active ingredient from the ambient environment, for instance atmospheric moisture when the product is exposed to the air, or the liquid phase of a liquid detergent when the product is incorporated in such a detergent.

Numerous ways of protecting active ingredient from the ambient environment are known. Some rely on a wholly liquid system. In U.S. Pat. No. 4,801,544, aqueous micelles of enzyme and surfactant are emulsified into a hydrocarbon solvent. In U.S. Pat. No. 4,906,396, enzyme is dispersed in a hydrophobic fluid, such as a silicone oil.

More usually, the enzyme is protected by a solid phase. In U.S. Pat. No. 4,090,973, solid surfactant is used. Often, however, a polymeric material is used. The enzyme or active ingredient may be dispersed in a polymeric matrix or it may be encapsulated by a polymeric shell formed around a core containing the active ingredient.

The solid polymeric material can be made by polymerisation of monomeric material in the presence of the active ingredient, but this is generally undesirable and normally the solid polymer of the matrix or shell is formed by depositing solid polymer from a solution of polymer. The polymer can remain chemically unchanged during the deposition from dissolved to solid form, the deposition being due primarily to a change in the solvent composition or properties. Alternatively, deposition can be caused by, accompanied by or followed by a chemical change in the polymer, such as neutralisation, complexing with another polymer, or cross linking. The formation of a solid polymer shell in this manner from a solution of polymeric material is generally termed coacervation.

Typical techniques for forming a polymer shell are described in, for instance, GB 1,275,712, 1,475,229 and 1,507,739, DE 3,545,803 and U.S. Pat. No. 3,591,090.

A particular problem arises when the active ingredient is an enzyme, especially an enzyme suitable for incorporation in detergents, because of the difficulty of preventing the enzyme losing activity before use.

Many different ways of encapsulating enzymes have been proposed. Some do not include coacervation. For instance GB 1,377,725 contacts atomised droplets of an aqueous slurry of enzyme with particles of starch. However there is a risk that the resultant coating will be discontinuous. It is therefore preferred to form the coating or matrix by deposition of solid polymer from a solution of polymer in which the enzyme is dispersed, i.e. by coacervation.

For instance in U.S. Pat. No. 3,838,007 droplets of enzyme dispersed in an aqueous solution of, for instance, gelatin are dispersed into water and then cross linked, to give cross linked particles of the gelatin containing the enzyme.

In JP-A-61254244, a typical process comprises mixing enzyme powder and silica into an aqueous solution of polyvinyl alcohol or other suitable polymer, dispersing the aqueous suspension into a non-aqueous liquid and adding acetone, so as to deposit the polymer as a wall around the enzyme particles. The product is said to have a particle size of around 50 to 2,000 um.

In U.S. Pat. No. 4,898,781, a dispersion is formed of enzyme powder in propylene glycol and aqueous polyvinyl alcohol and this dispersion is then converted into particles by various techniques. In one technique, the dispersion is introduced as droplets into an aqueous solution of cross linking agent, thereby solidifying by cross linking the polyvinyl alcohol. In another technique, the dispersion is dispersed into a hydrophobic solvent and then heated so as to drive off water and solidify the polyvinyl alcohol. The products are said to have a size of 20 to 1,000 um. Other techniques are described. JP-A-63105098 includes similar process description and many of the examples are identical. It proposed that the particles of enzyme in a covering of polyvinyl alcohol should be homogeneously dispersed in a liquid or gel detergent.

EP-A-356,240 (and U.S. Pat. No. 5,035,900) describes processes for encapsulating enzyme or other biologically produced material in a matrix of polymeric material by mixing the polymeric material with an aqueous liquor containing the biologically produced material (as a fermentation liquor or plant extract), dispersing this mixture in a water immiscible liquid and azeotroping the dispersion. The product can either be relatively coarse beads that can be recovered or a stable dispersion of small particles in the water immiscible liquid. Although this is a very useful recovery technique and provides some protection to the enzyme, additional stabilisation is desirable.

In EP-A-356,239 (which is equivalent to part of the disclosure in U.S. application Ser. No. 734,545, now U.S. Pat. No. 5,324,445 of 23rd Jul. 1991) we have described various compositions and processes primarily intended for the encapsulation of enzymes for liquid and other detergents. One type of product described therein comprises particles having a core comprising matrix polymer containing the enzyme, oil around the core and a polymer shell around the oil.

In particular, particles of a matrix polymer containing an active ingredient can be formed as a dispersion in oil and this dispersion can then be dispersed in an aqueous solution of an encapsulating polymer or blend of polymers and polymer deposition can then be caused to occur around the oil particles that contain the particles of matrix polymer that contain the active ingredient.

As explained in EP 356,239, it can be desirable for the matrix polymer to be a salt formed between ammonia or other volatile amine and a polymer derived from ethylenically unsaturated carboxylic acid. The matrix polymer can be formed or introduced as an aqueous solution of the salt with a volatile amine and this dispersion can then be subjected to azeotroping to drive off water and the volatile amine, so as to solidify the polymer wholly or partially in the free acid form. The solid polymer will be less hydrophilic than the starting amine salt and so will provide some impermeability to protect the encapsulated enzyme from moisture. The combination of this relatively impermeable matrix, the outer polymer shell, and the intervening oil would be expected to provide excellent stability to the enzyme. Although the system does give significant improvements, there is still some loss of activity.

It would be desirable to be able to provide coacervated particles that could more reliably protect any active ingredient in the matrix from exposure to moisture during manufacture and subsequent storage.

A particulate composition according to the invention comprises particles having a substantially anhydrous core comprising one or more particles of a matrix polymer containing active ingredient and a layer of hydrophobic oil around the matrix polymer particle or particles, and a shell of polymer around the oil layer, wherein the solid matrix polymer is sufficiently hydrophobic that it will partition preferentially into the oil rather than into water.

By referring to partitioning into "water", we are referring in particular to the partitioning of the solid matrix polymer into the aqueous solution from which the shell polymer was formed. In many instances, the partitioning properties into ordinary water do, however, give a useful guide.

If the encapsulating polymer was deposited from a neutral solution, then it is more convenient to define the matrix polymer as partitioning into the oil in preference to water, but if the encapsulating polymer was mixed with the dispersion in the form of an alkaline solution then the relative partitioning effect should be determined with respect to an alkaline solution corresponding to the alkalinity of that solution in order to allow for any solubilisation of the polymer by salt formation with the alkali of the encapsulating solution.

A process according to the invention for producing encapsulated particles comprises providing an aqueous solution of encapsulating polymeric material that can be caused to deposit as a solid shell about particles dispersed in the solution, providing a substantially anhydrous dispersion in oil of particles of a matrix polymer containing active ingredient, dispersing this substantially anhydrous dispersion of matrix polymer particles containing active ingredient in oil into the aqueous solution, and causing a solid polymer shell to form around droplets of the matrix particles in oil, wherein the matrix polymer partitions into the oil in preference to the aqueous solution of encapsulating polymeric material.

The invention is based on our realisation that, even though the matrix polymer in EP 356,239 was relatively nonhydrophobic, it was considerably more hydrophilic than the oil with the result that the aqueous solution of encapsulating polymer and the matrix polymer particles were attracted to one another with undesirable consequences. Since the formation of the dispersion generally involved homogenising the polymer-in-oil dispersion into the aqueous solution encapsulating polymer, the act of forming the dispersion was able to result in intimate and prolonged contact between the polymer particles and the aqueous solution.

It seems that during this contact there can be migration of water from the solution into the matrix polymer, with the result that, even though the polymer particles had been dried by azeotroping, the particles that were then encapsulated within the outer shell contained trapped moisture. This can be undesirable for enzymes and other active ingredients.

Also, there can be some migration of the enzyme or active ingredient out of the matrix polymer and into the aqueous solution, thereby losing the benefit of trapping the enzyme initially in the matrix polymer.

Finally, because of the attraction of the aqueous solution to the matrix polymer, the encapsulating polymer could tend to deposit direct on to the matrix polymer, without any oil trapped between the matrix polymer particle and the encapsulating polymer shell. Since the oil is capable of hindering the inward migration of moisture, this also was undesirable.

In the invention, we use a matrix polymer that is so hydrophobic that it partitions preferentially into the oil rather than into the aqueous solution of encapsulating polymer.

This therefore reduces the risk of moisture migrating from the aqueous solution into the matrix, and it reduces the risk of enzyme or active ingredient migrating out of the matrix into the aqueous solution. Because the aqueous solution is incompatible with both the hydrophobic oil and the matrix polymer there is increased tendency for the encapsulating shell to be formed around a layer of oil, rather than in direct contact with a matrix polymer particle. Finally, the increased hydrophobic properties of the matrix polymer reduce still further the tendency for migration of moisture into the polymer.

In a preferred process of the invention, the substantially anhydrous dispersion of particles of the matrix polymer in oil is made by providing a dispersion in oil of an aqueous solution of matrix polymeric material containing enzyme or other active ingredient, subjecting this dispersion to distillation to provide a substantially anhydrous dispersion in oil of particles of matrix polymer containing active ingredient, and during or after the distillation converting the polymer solution into a solid polymer.

The initial aqueous solution of matrix polymeric material can be made by dissolving the polymeric material in water or other aqueous solution in which it is soluble, and dispersing or dissolving the active ingredient in the solution. In another process, the dispersion is made by reverse phase polymerisation of a water soluble monomer or monomer blend in the presence of the active ingredient.

The conversion of the droplets of polymer solution into solid polymer particles can be brought about by various techniques. For instance, it can be due merely to evaporation of solvent. It can be due to chemical modification even though solidification may include another cause. This modification should produce a polymer that is insoluble in water and that will partition into the oil in preference to the aqueous solution of encapsulating material.

One form of chemical modification can involve cross linking, for instance a cross linking agent can be included in the polymer solution and will cause cross linking during or after the azeotroping.

Another, and preferred, form of chemical modification comprises converting a polymer that is in salt form into free base or free acid form. Thus a polymer containing amino groups can be present initially as a water soluble salt but can be insolubilised by conversion to the free base, or polymer that is in anionic soluble salt form can be insolubilised by conversion to the free acid. Such conversion can be partial or complete. Preferably the salt forming moiety is volatile with the result that conversion to the free acid or free base can be achieved during distillation. Amine (including ammonium) salts of anionic polymer are preferred. The modification normally occurs during or after azeotroping and renders the matrix less permeable, e.g. to liquid detergent concentrate.

Another way of converting the matrix polymer to solid form is by selecting a hydrophobic polymer from the class known as "low critical solution temperature" (LCST) polymers. The process by which these can be used for the matrix is substantially the same as the process by which they can be used for forming the encapsulating shell, and this is described in more detail below. In brief, a characteristic of such polymers is that they can be insolubilised by heating to a critical temperature (for instance as can happen during the distillation stage) and a depressant for the temperature of insolubilisation (for instance a water miscible non-solvent or an electrolyte) can be added to stabilise the solid form at a lower temperature. This is all described in more detail below.

Other coacervating techniques can be used.

In this specification, and in particular in the following discussion of the formation of the polymer shell, we use the term "coacervation" and "coacervating polymer" in the general sense described above, namely any mechanism by which a polymer can be converted from a solution form to a solid, encapsulating, form. Accordingly, for convenience, we refer below to the encapsulating polymer as a coacervating polymer and we refer to the aqueous solution of this as an aqueous coacervating solution.

By saying that the matrix polymer partitions into the oil in preference to the aqueous solution of coacervating polymer, or other water phase, we mean that the polymer particles will be preferentially attracted to the oil phase rather than to the aqueous phase. One simple way of demonstrating whether or not the matrix polymer does preferentially partition into the oil phase is to incorporate some water soluble dye into the matrix polymer and then to disperse vigorously a dispersion of the dyed polyer particles in the oil into the aqueous phase, and then to allow the dispersion to phase separate. If substantially all the dye has remained in the polymer particles, this shows that there was substantially no contact between the polymer particles and the water, and that the polymer particles therefore partition preferentially into the oil phase. However if the water phase is significantly dyed, this shows that the polymer particles have partitioned significantly or preferentially into the aqueous phase.

The oil can be any hydrophobic, water immiscible, liquid. Examples are aliphatic, cycloaliphatic, aromatic and naphthenic oils, vegetable oils and silicone oils.

Because the oil is hydrophobic, and because the matrix polymer also is hydrophobic and is attracted to the oil in preference to the water, a film or larger amount of oil is held around each polymer particle during the formation of the coacervate, and the coacervate coating is formed as an outer shell around this inner shell of oil. This has two significant advantages:

Firstly, there is little or no direct contact between the aqueous coacervating phase and the substantially anhydrous matrix polymer. As a result, there is little or no opportunity for water to migrate into the substantially anhydrous matrix polymer during the formation of the coacervate coating or for active ingredient in the matrix polymer to migrate out into the coacervating solution. In particular, the coacervation can be conducted without raising the moisture content of the matrix polymer.

Secondly, the active ingredient in the matrix polymer is protected from its surroundings not only by the outer coacervate coating but also by the inner layer of hydrophobic oil. Thus even if the coacervate coating has a tendency to allow permeation by moisture, the inner shell of hydrophobic oil between the coacervate and the matrix polymer will reduce or eliminate any risk of transfer of moisture from outside the particle to the matrix polymer or transfer of water soluble active ingredient in the matrix polymer to outside the coacervate coating.

In order that the polymer does partition preferentially into oil, it is necessary for it to be much more hydrophobic than, for instance, the acrylic acid-ammonium acrylate polymer proposed in EP 356239.

As mentioned above, the matrix polymer is generally provided by insolubilising a polymer that was initially provided as an aqueous solution. Any modification that achieves this insolubilisation can be used but preferably the modification is reversible so that the polymer can then be solubilised when it becomes necessary to facilitate release of active ingredient from within the particles into water. The modification can be achieved chemically or physically. When the modification is achieved chemically, the initially soluble polymer is preferably a copolymer of water soluble ionic monomer with water insoluble monomer, in which event the reversible insolubilisation will preferably comprise converting some or all of the ionic monomer groups to free acid or free base monomer groups.

Suitable monomers are ethylenically unsaturated monomers. Ionic monomers are preferably anionic monomers groups that include sulphonic or, preferably, carboxylic acid groups. Preferred monomers include methacrylic and acrylic acids. The anionic groups may be present in the soluble polymer as alkali metal or amine salts and may be converted to free carboxylic acid groups in the insolubilisation reaction. This can be achieved by acidification with hydrochloric acid or other suitable acid but preferably the anionic group is present as a salt of a volatile amine (e.g., ammonia) and the acidification is achieved by heating the polymer sufficient to volatilise the ammonia or other amine. This heating can occur during the distillation step. Although anionic groups are preferred as the ionic groups, cationic groups such as dialkylaminoalkyl (meth)-acrylate or amide acid addition or quaternary ammonium salt can be used.

The ionic groups must be copolymerised with hydrophobic water insoluble monomer. Suitable hydrophobic ethylenically unsaturated monomers are hydrocarbon monomers such as styrene and alkyl-substituted styrenes, alkyl acrylates and methacrylates (for instance methacrylate) and vinyl acetate.

The amount of hydrophobic monomer will generally be from 40 to 95% by weight, with the balance to 100% being the ionic monomer. However small amounts (e.g., up to 20%) of other monomers that are neither ionic nor hydrophobic may be included, an example being vinyl pyrrolidine.

The matrix polymeric material can be made by solution polymerisation in the organic solvent or by oil-in-water emulsion polymerisation, followed by addition of sufficient alkali to solubilise the aqueous polymer in the conventional manner. Active ingredient can be dispersed or dissolved in the polymerising mixture before polymerisation, but preferably is dispersed or dissolved into a solution of the polymeric material after polymerisation. The polymer can be made as a water soluble salt by reverse phase polymerisation, e.g., in the hydrophobic oil that is used in the encapsulation process.

If the polymer was not formed as a reverse phase emulsion, the resultant solution of polymer containing active ingredient can be dispersed into the desired hydrophobic oil (or the polymer can be dispersed in the oil and the active ingredient then added) in the presence of suitable dispersion stabiliser that can be a water-in-oil emulsifier and/or an amphipathic polymeric stabiliser. Suitable emulsifiers, stabilisers and oils are described in, for instance, EP 128,661, EP 284,366 and EP 284,367. Emulsification can be achieved by homogenisation with a Silverson or other homogeniser.

The dispersion of aqueous polymer and active ingredient in oil can subsequently be subjected to distillation under reduced pressure until substantially all the water has been removed. If the active ingredient is temperature sensitive, the reduced pressure should be sufficiently low that the distillation occurs at a safe temperature, for instance below 30° C. Anionic monomer is preferably present as ammonium salt, in which event the dispersion can be heated briefly to a temperature and for a time sufficient to drive off most of the ammonia but insufficient to damage any heat-sensitive active ingredient in the matrix polymer.

The resultant dispersion of dry polymer particles in oil can then be dispersed into an aqueous solution of coacervating polymeric material, for instance by emulsification using a Silverson homogeniser. The particle size can be controlled in known manner by appropriate selection of the emulsification conditions and generally is below 20 μm, usually below 10 μm, although if desired the process can be used to make larger particles, e.g., up to 100 um or 500 um. The size will usually be above 0.3 μm, e.g. up to 3 μm If the particle size of the resultant oil-in-water dispersion is small, each oil droplet may only contain one particle of matrix polymer, with the result that the core of the final product comprises a single matrix polymer particle surrounded by some oil. However each droplet, and therefore each core, often includes several matrix polymer particles dispersed in oil.

Coacervation can be by any known technique, for instance any of those mentioned or used in EP 356,239, but is preferably by use of "low critical solution temperature" (LCST) polymers. Coacervation can be brought about solely by heating as described in U.S. Pat. No. 3,244,640 but preferably coacervation is brought about by heating followed by the addition of a depressant. In particular, a process for encapsulating by coacervation particles each comprising matrix polymer (containing active ingredient) and an outer layer of oil can be performed as described in our Application filed today Ser. No. 08/196,230, now abandoned that claims priority from British Application 9110407.5. This process comprises

- providing an aqueous solution of a LCST polymer that has a temperature of reversible insolubilisation (TRI) in that solution of T1,
- forming a dispersion of the particles in that solution at a temperature T2 that is below T1,
- heating the dispersion to a temperature above T1 and thereby precipitating the LCST polymer as a coascervate around the particles, then
- adding a TRI depressant to the solution and thereby reducing the temperature of reversible insolubilisation of the LCST polymer in that solution to a temperature T3 that is lower than T1, and
- either cooling the dispersion to a temperature between T3 and T1 and maintaining the dispersion at a temperature between T3 and T1,
- or separating the particles from the dispersion while at a temperature above T3.

The TRI depressant, and its amount, are selected to give the desired depression in the temperature of reversible insolubilisation. Preferably it is an electrolyte.

A wide variety of electrolytes can be used but since satisfactory results are obtained with simple inorganic salts, it is generally preferred to use them as part or all of the electrolyte. Suitable salts include sodium, potassium, ammonium, calcium, magnesium and aluminium salts, particularly of carbonate, sulphate, chloride and nitrate. Some or all of the electrolyte can be anionic surfactant, for instance of the type conventionally present in a liquid detergent concentrate.

Typical amounts of salt that should be added are 2 to 30% based on the aqueous composition, or such as to give a 15:1 to 1:15 weight ratio of polymer:salt. The amount is preferably sufficient for T3 to be at least 5° C. below the anticipated lowest temperature of storage. As mentioned, some electrolyte can be present in the initial solution, typically in an amount of 0 to 5% based on the initial solution, provided this does not depress T1 too much.

Generally T1 is at least 5° C. higher than the anticipated temperature of usage, for instance the temperature of the dilution water into which the particles are to be dissolved.

Although we prefer to use an electrolyte for depressing the reversible insolubilisation temperature, any other material that has the desired depressant effect can be used. Generally they can all be characterised as being water-miscible non-solvents (in the absence of significant amounts of water) for the relevant LCST polymer. Examples include organic liquids such as lower alcohols, glycols and non-ionic surfactants. Particular examples are ethanol, glycerol, ethylene glycol, mono propylene glycol and ethoxylated octyl or nonyl phenol surfactants.

The LCST polymer can be a naturally occurring polymer such as certain cellulose derivatives, such as the methyl, hydroxy propyl, and mixed methyl/hydroxy propyl cellulose ethers. However it is generally preferred for the LCST polymer to be a synthetic polymer formed by polymerisation of what can be termed an LCST monomer either as a homopolymer or as a copolymer with a hydrophilic monomer that is present in an amount insufficient to cause T1 to be unacceptably high. Suitable LCST monomers include N-alkylacrylamide, N,N-dialkylacrylamide, diacetone acrylamide, N-acryloylpyrrolidine, vinyl acetate, certain (meth) acrylate esters (especially hydroxypropyl esters), styrene, and various other vinyl monomers, especially N-vinylimidazoline and the like.

When the LCST polymer is a copolymer, the comonomer is usually hydrophilic and can be non-ionic or ionic. Suitable non-ionic monomers include acrylamide, hydroxyethyl acrylate, vinyl pyrollidone, or hydrolysed vinyl acetate.

Anionic or cationic monomer can be used in place of or in addition to the non-ionic comonomer to form a copolymer or terpolymer with the LCST monomer respectively. Suitable anionic monomers include ethylenically unsaturated carboxylic or sulphonic acid monomers, for example (meth) acrylic acid and alkaline salts thereof, and 2-acrylamido methyl propane sulphonic acid. Suitable cationic monomers include dialkylaminoalkyl (meth)acrylates and acrylamides as acid addition or quaternary ammonium salts, for example dialkylaminoethyl (meth)acrylate acid addition salts. One beneficial effect resulting from the use of cationic or anionic comonomer or termonomer is that their presence can prevent the coagulation and subsequent phase separation of the encapsulated particles which may occur in particularly high salt environments such as may exist in certain detergents.

The method relies upon the reversible insolubilisation by temperature change of an LCST polymer to form a coacervate coating, followed by the addition of a TRI depressant to modify the properties of the coating in a beneficial manner. Since the initial insolubilisation is by temperature change, this can be conducted homogeneously througout the composition and so can yield very uniform coacervation.

An essential modification of the coating is that the TRI depressant reduces the temperature of reversible insolubilisation of the coating. This means that the temperature of the solution can be cooled below the temperature at which the coacervate coating was first formed without the coating being solubilised. This permits handling, storage and recovery at ambient temperatures.

Another modification is that the addition of the TRI depressant can tend to change other physical properties of the coating of the LCST polymer. In particular, it is easily possible to select an LCST polymer that forms a much harder and less permeable coating in the presence of an added electrolyte (as the TRI depressant) than in its absence. Thus the addition of the electrolyte will generally both reduce the temperature of reversible insolubilisation of the polymer and will render the coating much harder and less permeable than it would be in the absence of the electrolyte.

However, the effect is reversible since when the concentration of TRI depressant is sufficiently reduced, the temperature of reversible insolubilisation will then rise again to, or at least towards, the initial temperature T1 of reversible insolubilisation. Also, if the TRI depressant hardened the coating, the coating may tend to revert to its original softer and more permeable texture.

The temperature T1 of reversible insolubilisation of the LCST polymer is the temperature at which the polymer will become insoluble if the solution containing the polymer is heated past T1 or will become soluble if insoluble polymer in that aqueous solution is cooled below that temperature. The temperature of reversible insolubilisation is generally reasonably abrupt, but may extend over a few degrees or more. Naturally T3 must be sufficiently low that any range for T1 does not significantly overlap the range for T3, which is the corresponding temperature for the polymer in the aqueous solution containing the TRI depressant. It should be noted that T1 and T3 relate to the polymer in the particular aqueous solution in which it exists. Thus, in the invention, the initial aqueous solution can contain some electrolyte or other TRI depressant in which event T1 in that solution will generally be lower than it would be if the initial solution had been free of electrolyte or other depressant, but additional electrolyte or other depressant is then added to reduce the temperature of reversible insolubilisation to T3.

T1 is generally at least 25° C. and often at least 30° C. and frequently is in the range 45° to 80° C. but can be as high as 100° C. Some polymers require the presence of some electrolyte in order to bring T1 in the initial solution down to a convenient value, e.g. below 100° C.

T3 is generally at least 5° C. lower than T1 and is preferably at least 10° C. and often at least 20° C. below T1. When the particles are to be stored in aqueous electrolyte, T3 should be below the probable storage temperature. Preferably T3 is 0° C., that is to say the coating will never dissolve in liquid water, but higher values of T3, such as 5° C. or even 10° C., can be acceptable in many instances.

Irrespective of how the coacervation of the shell is achieved, the choice of coacervate shell must be such as to allow eventual release of active ingredient from within the matrix when the product is exposed to selected conditions, whilst preventing release prior to that stage. For instance, if the particles are in the form of dry powder the coacervate shell should reduce ingress of ambient moisture sufficient to prevent significant deactivation of the active ingredient but upon exposure to dilution water or an appropriate chemical reagent (for instance dilute alkali), the shell should permit adequate permeation through the shell and from the matrix into the surrounding liquor.

When the composition is in the form of a dispersion in liquid, the shell should prevent permeation of that liquid through the shell but should be capable of permitting permeation when the liquid is changed, for instance when it is diluted. When, as is preferred, the composition is in the form of a liquid detergent in which the encapsulated particles are dispersed, the shell should be such as to prevent substantially permeation of the alkaline liquid through the shell but should be such as to permit permeation by wash water, often warm wash water, when the liquid detergent is diluted in wash water.

Suitable coacervating polymers can be the LCST polymers mentioned above and the coacervating polymers that have previously been proposed for, for instance, the coacervate shell around enzyme particles, especially enzyme particles that are to be dispersed into a liquid detergent. Suitable materials are described in, inter alia, EP-A-356239. Cross linked pva is suitable.

A wide variety of active ingredients can be encapsulated by the described technique including dyes (for pressure sensitive paper), agricultural chemicals, perfumes, flavours, condiments, essential oils, bath oils, bleaching agents, and enzymes. Suitable agricultural chemicals are water insoluble pesticides (e.g. herbicides and insecticides) that would otherwise need to be formulated as, for instance, an emulsifiable solution in oil. The invention is of particular value when applied to the encapsulation of enzymes, and in particular detergent enzymes, i.e. enzymes of the type that are useful for inclusion in laundry or other detergent compositions.

When the particle size is small, e.g. below 20 um, the particulate composition is generally provided as a dispersion in the liquid medium, for instance a liquid detergent. When the particle size is larger, for instance above 50 um and especially above 100 um, the particles can be recovered as dry particles.

The liquid or dry composition can be substantially storage stable due to the protection provided by the matrix polymer, the oil layer and the encapsulating coacervate shell. Upon mixing with water, or other appropriate change in the ambient conditions, the outer shell disintegrates or swells sufficient to allow penetration of the oil layer and release of the active ingredient from within the matrix, possibly after chemical reversion of that matrix to render it more hydrophilic. For instance, if, as is preferred, the matrix polymer is the acid form of an anionic polymer, exposure to alkaline wash water will tend to solubilise it.

Suitable proportions of active ingredient: matrix polymer are 1:100 to 1:0.5 on a dry weight basis, whilst the matrix/active ingredient:coacervate polymer ratio is generally from 1:60 to 5:1 on a dry weight basis. The amount of oil encapsulated within the particles is generally from 20 to 97% based on the dry weight of the particles.

When the active ingredient is an enzyme for detergents and the composition is a liquid detergent, its formulation can be conventional for enzyme-containing liquid detergents except that the enzyme is included in the form of the described particles. Typical liquid detergents comprise, in % by weight,

| Component | Soap Built | Citrate Built |
|---|---|---|
| Linear alkyl benzene sulphonate | 10 | 10 |
| Alkyl ether sulphate | 2 | 4 |
| Soap | 14 | 1 |
| Alcohol ethoxylate | 13 | 6 |
| Sodium hydroxide (Triethanolamine) | 2(5) | 1(0) |
| Sodium xylene sulphonate | 1 | 5 |
| Sodium sulphate | 0 | 1 |
| Sodium carbonate | 0 | 2 |
| Tri-sodium citrate | 1 | 6 |
| Ethanol | 5 | 1 |
| Monopropylene glycol | 3 | 3 |
| Water | 44 | 60 |

EXAMPLE 1

Preparation of LCST copolymer

Diacetone acrylamide (1 part) and acrylamide (0.4 part) were dissolved in 1% aqueous sodium acetate at pH 6.5 (4.2 parts). This solution was purged with nitrogen for 45 min in a lagged reaction vessel fitted with a mechanical stirrer.

Polymerisation was initiated by addition of 5% aqueous ammonium persulphate (500 ppm) followed by 5% aqueous sodium metabisulphite (500 ppm). The course of the reaction was monitored by recording the temperature. After 30 min, the temperature had risen from 20° C. to a constant value of 70° C.

The mixture had become white and opaque and more viscous. On cooling, a pale yellow clear viscous solution (25%) of Polymer A resulted.

By measuring the onset of turbidity of a 10% aqueous solution of Polymer A, the lower critical solution temperature (or temperature of reversible insolubilisation), was found to be 30° C.

EXAMPLE 2

Savinase plus matrix polymer dispersion in oil

An aqueous phase is formed by mixing 160 g 30% solution of a copolymer of styrene and ammonium acrylate with 140 g liquid Savinase preparation (12 g active protease enzyme, supplied by Novo-Nordisk A/S) and its pH is adjusted to 9.0).

The oil phase is formed by mixing 9 g polymeric inverse emulsifier, 12.7 g 60% amphipathic polymeric stabiliser, 107.9 g non-volatile hydrocarbon oil and 31.9 g volatile hydrocarbon solvent.

The aqueous phase is added to the agitated oil phase and then homogenised with a high shear Silverson mixer whilst maintaining the temperature of the emulsion below 40° C. After 30 minutes emulsification, extra 138.5 g of the volatile hydrocarbon solvent is added as a diluent.

The resultant emulsion is warmed to 30° C. and water/solvent mixture distilled under reduced pressure at a constant temperature about 30° C. The volume of water and solvent removed is monitored and distillation continued until no further water is collected in the distillate and then the temperature is allowed to rise to 110° C. under vacuum to remove remaining solvent. The dried dispersion is held at 100° C. for 15 minutes to drive off ammonia so as to render the matrix polymer insoluble in water.

The contents of the flask are cooled. The dispersion of Savinase plus polymer particles in oil (40% solids) is stable and having an average particle diameter of less than 1 μm.

EXAMPLE 3

Microencapsulation of dispersion-in-oil obtained in Example 1

The dried enzyme/polymer dispersion (33 parts) from Example 1 is added with high shear mixing to 100 parts 10% solution of Polymer A at pH 4 from Example 1.

The resultant smooth o/w emulsion is warmed in a water bath to 40° C. and held at this temperature for 15 min. Aqueous sodium sulphate (10%, 5 parts) is added and the mixture then allowed to cool slowly to 20° C. A stable microcapsule suspension in water is obtained having average particle size diameter of about 1 micron.

EXAMPLE 4

The Savinase dispersion in oil prepared as in Example 2 (40 parts) was mixed with gentle agitation into 400 parts of an aqueous solution of poly-(vinyl alcohol) (2%; 74% hydrolysed; $M_n$ 25000) adjusted to pH4 with dilute hydrochloric acid.

This mixture of oily droplets (containing the dispersed particles of hydrophobised enzyme) was warmed to 42° C. over 15 mins and held at this temperature for a further 30 mins. The outer shell of coacervated poly-(vinyl alcohol) which could be seen clearly under the microscope to surround the oil droplets (average particle size 300 micron) was cross-linked by addition of 1 part of 50% aqueous glutaraldehyde solution, pH adjusted to 3 by a few drops of concentrated hydrochloric acid and the mixture stirred gently for 5 h at 42° C.

The capsules produced by this method were recovered by sieving through a fine nylon mesh were physically strong and could be recovered in a dry form by aerial drying. An enzyme assay for protease activity after physical rupture of these capsules in dilute aqueous detergent at pH9 showed 88% of the protease activity present in the oil protease suspension from Example 2.

A modern heavy duty compact powder detergent was formulated. To one half of this powder detergent was added the capsules-containing Savinase as described above. Savinase 6.0T granules (Novo-Norsik A/S Denmark) were added to the other half of the powder detergent to give an equal protease activity.

Both enzyme containing formulations were subjected to an accelerated storage stability test by being placed in open jars at 37° C. and 70% relative humidity. Protease assays of both formulations showed there to be more than double the activity in the capsules formulation than in the one made with normal granulated Savinase 6.0T.

EXAMPLE 5

The process of Example 4 was repeated but to a smaller particle size and the microcapsules containing the Savinase were added to a soap built liquid detergent and accelerated storage stability tests performed at 30° C. compared with a control which contained unprotected Savinase at the same protease activity. After 15 days, the capsule containing liquid detergent contained 2.5 times the protease activity than the unprotected control.

EXAMPLE 6

Demonstration of partitioning and dissolution characteristics

Using the azeotropic distillation process as described in Examples 1 and 2, a dispersion comprising a dispersed phase of a styrene/acrlic acid polymer in a paraffinic oil is prepared. A water soluble polymeric dye (blue dextran) is incorporated into the polymer particles at 0.5% wt as a marker.

An experiment is performed to see if the polymer particles would activate (i.e. partition into and dissolve in the aqueous phase) on contact of matrix polymer plus dye dispersion with water at two different pH values.

The dispersion (1 part) was added with high shear mixing to water (99 parts) at either pH4 or pH9. After 2 min mixing, the turbid mixture was centrifuged with these results:

| pH | Observation | Conclusion |
| --- | --- | --- |
| 4 | Blue colour associated with oily layer Solution clear colourless | No activation |
| 9 | Distinct blue solution with a trace of oil on surface | Activation |

Therefore it can be seen that under acidic conditions the matrix polymer remains water insoluble and the particles stay in the oil phase. Thus the polymer particles are considered to partition into the oil phase at pH4, which is the pH4 prevailing at the time the dry polymer-in-oil dispersion is mixed into the aqueous coacervating solution. However when exposed to dilute alkali at pH9 (e.g. as would apply after permeation of the coacervate shell in dilute laundry wash water) the matrix polymer dissolves and releases its active ingredient.

We claim:

1. A particulate composition comprising particles having a substantially anhydrous core comprising one or more particles of a matrix polymer containing active ingredient and a layer of hydrophobic oil around the matrix polymer particle or particles, and a coacervate shell around the oil layer formed by coacervation of coacervate polymer wherein the solid matrix polymer is sufficiently hydrophobic that it will partition preferentially into the oil rather than into water.

2. A process for producing encapsulated particles comprising selecting a matrix polymer, providing a dispersion in oil of an aqueous solution of the matrix polymer containing active ingredient, subjecting this dispersion to distillation to provide a substantially anhydrous dispersion in oil of particles of matrix polymer containing active ingredient and during or after the distillation converting the matrix polymer into a solid polymer, providing an aqueous solution of encapsulating polymeric material that can be caused to deposit as a solid shell about particles dispersed in the solution, dispersing the substantially anhydrous dispersion of matrix polymer particles containing active ingredient in oil into the aqueous solution and causing a solid coacervate polymer shell to form around droplets of the matrix particles in oil, wherein the polymer which is selected as matrix polymer is a polymer which partitions into the oil in preference to the aqueous solution of encapsulating polymeric material.

3. A process according to claim 2 in which the matrix polymer is an ionic polymer which is soluble in water when present in salt form but is insoluble when in free base form or free acid form, and in which the conversion of the matrix polymer into a solid polymer is achieved by converting the soluble salt into the insoluble free acid or free base polymer.

4. A composition according to claim 1 in which the coacervate shell of polymer is cross linked.

5. A composition according to claim 1 in which the coacervate shell of polymer is formed of polyvinyl alcohol.

6. A composition according to claim 1 in the form of dry particles having a size above 50 um.

7. A composition according to claim 1 that is a liquid composition comprising a substantially stable dispersion in a liquid of the particles.

8. A composition according to claim 7 which is a liquid detergent concentrate wherein the active ingredient is an enzyme useful in detergents.

9. A composition according to claim 7 in which the particles are below 20 um in size.

10. A process according to claim 3 in which the matrix polymer is formed by polymerisation of ethylenically unsaturated monomers comprising water soluble ionic monomer and water insoluble hydrophobic monomer.

11. A process according to claim 3 in which the solid matrix polymer is a copolymer of hydrophobic monomer with anionic monomer in substantially free acid form.

12. A process for producing encapsulated particles comprising selecting a matrix polymer, providing an aqueous solution of encapsulating polymeric material that can be caused to deposit as a solid shell about particles dispersed in the solution, providing a substantially anhydrous dispersion in oil of particles of the matrix polymer containing active ingredient, dispersing this substantially anhydrous dispersion of matrix polymer particles containing active ingredient in oil into the aqueous solution, and causing a solid coacervate polymer shell to form around droplets of the matrix particles in oil, and in which the selected matrix polymer partitions into the oil in preference to the aqueous solution of encapsulating polymeric material.

13. A process according to claim 12 in which the encapsulated particles are combined with a liquid to form a substantially stable dispersion of the particles in the liquid.

14. A process according to claim 2 in which the solution of matrix polymer is a solution of an anionic polymer in the form of a salt with a volatile amine, and the amine is evaporated during or after the distillation.

15. A process according to claim 2 in which the formation of the solid polymer shell comprises the cross linking of polyvinyl alcohol.

16. An encapsulated particle made by the process of claim 12.

17. A process according to claim 2 in which the causing a solid coacervate polymer shell to form comprises crosslinking polymer.

18. A process according to claim 2 in which the coacervate polymer is polyvinyl alcohol.

19. A process according to claim 2 in which the coacervate particles are dry and have a size above 50 μm.

20. A process according to claim 13 in which the liquid composition is a liquid detergent.

21. A process according to claim 13 in which the active ingredient is an enzyme useful in detergents.

22. A process according to claim 13 in which the particles are below 20 μm in size.

23. A process according to claim 2 in which the encapsulated particles are combined with a liquid to form a substantially stable dispersion of the particles in the liquid.

24. A process according to claim 23 in which the liquid composition is a liquid detergent.

25. A process according to claim 23 in which the active ingredient is an enzyme useful in detergents.

26. A process according to claim 23 in which the particles are below 20 μm in size.

27. An encapsulated particle made by the process of claim 2.

* * * * *